United States Patent [19]

Clarke et al.

[11] Patent Number: 5,770,610

[45] Date of Patent: Jun. 23, 1998

[54] MELATONIN AGONISTS FOR USE IN THE TREATMENT OF BENIGN PROSTATIC HYPERPLASIA (BPH)

[75] Inventors: David Oakley Clarke, Indianapolis; William Henry Jordan, Greenfield; Lisa Ann Shipley, Fishers, all of Ind.

[73] Assignee: Eli Lilly and Company, Indianapolis, Ind.

[21] Appl. No.: 661,535

[22] Filed: Jun. 11, 1996

Related U.S. Application Data

[60] Provisional application No. 60/000,203 Jun. 14, 1995.

[51] Int. Cl.[6] .................................................. A61K 31/405
[52] U.S. Cl. ............................................................ 514/415
[58] Field of Search ...................................... 514/415, 416

[56] References Cited

U.S. PATENT DOCUMENTS

| 4,600,723 | 7/1986 | Short et al. ................................ 514/416 |
|---|---|---|
| 4,614,807 | 9/1986 | Flaugh ...................................... 548/507 |
| 4,997,845 | 3/1991 | Flaugh ...................................... 514/415 |
| 5,196,435 | 3/1993 | Clemens et al. ......................... 514/284 |
| 5,242,941 | 9/1993 | Lewy et al. .............................. 514/416 |

FOREIGN PATENT DOCUMENTS 525296  10/1993  European Pat. Off. .

OTHER PUBLICATIONS

Chem. Pharm Bull., 40(4), 1066–1068 (1992).
Life Sciences, vol. 10, Part I, pp. 259–269 (1971).
Journal of Endocrinology (1990) 126, 431–435.
J. Endocr. (1988) 116, 43–53.
Craig et al. "Modern Pharmacology", published by Little, Brown and Company (Boston), p. 16, 1982.

*Primary Examiner*—Raymond Henley, III
*Attorney, Agent, or Firm*—Robert D. Titus; David E. Boone

[57] ABSTRACT

The present invention provides a method for the treatment of benign prostatic hyperplasia using various melatonin agonists.

2 Claims, No Drawings

MELATONIN AGONISTS FOR USE IN THE TREATMENT OF BENIGN PROSTATIC HYPERPLASIA (BPH)

This application claims the benefit of U.S. Provisional Application No. 60/000,203, filed Jun. 14, 1995.

BACKGROUND OF THE INVENTION

Melatonin, N-[2-(5-methoxy-3-indolyl)ethyl]-acetamide, is a pineal gland hormone which has ovulation inhibitory activity, Chu et al., *Endocrinology*, 75, 238 (1964), as well as some activity against MCF-7 human breast cancer cells, Blask et al. *J. Neural. Transm.* [Supp.], 21, 433 (1986) and for the treatment of mammalian breast carcinoma, Blask et al., *Neuroendocrinol. Lett.*, 9(2), 63 (1987). Furthermore, melatonin has been known to expedite recovery from "jet lag syndrome", Arendt et al., *Ergonomics*, 30, 1379 (1987), to cause sleep, Waldhauser et al., *Psychopharmacology*, 100, 222 (1990) and to minimize disturbances in circadian rhythms of bodily performance and function, U.S. Pat. Nos. 4,600,723 and 5,242,941. Additionally, certain formulations containing melatonin have been indicated for the treatment of benign prostatic hyperplasia (EP 565296 A1 931013).

Several melatonin agonists of the formula

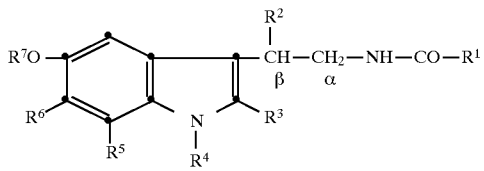

wherein
$R^1$ is hydrogen, $C_1$–$C_4$ alkyl or $C_1$–$C_4$ alkoxy;
$R^2$ is hydrogen or $C_1$–$C_4$ alkyl;
$R^3$ is hydrogen or methyl;
$R^4$ is hydrogen, haloacetyl, $C_1$–$C_5$ alkanoyl, benzoyl or benzoyl substituted with halo or methyl;
$R^5$ and $R^6$ are individually hydrogen or halo; and
$R^7$ is hydrogen or $C_1$–$C_4$ alkyl;
have also been prepared and shown to possess ovulation inhibition activity (see U.S. Pat. Nos. 4,997,845 and 4,614,807). Such analogues are also stated to be active in treating hormonally dependent breast carcinomas in U.S. Pat. No. 5,196,435. However, none of these agonists were previously shown to possess activity in treating benign prostatic hyperplasia. Finally, European Patent Application 513,702 discloses that melatonin and compounds of the formula

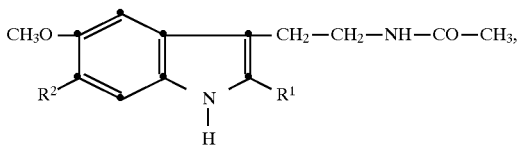

wherein $R^1$ and $R^2$ are the same or different and are hydrogen or halogen can be used in treating sleep disorders and in pre-anesthetic medication. Again, such disclosure does not teach or suggest the use of melatonin agonists for treating benign prostatic hyperplasia.

It is an object of this invention to provide a new method for the prevention and treatment of benign prostatic hyperplasia (BPH) by employing certain known melatonin agonists. The following classes of melatonin agonists have been reported and are useful in the method of the present invention: 1) N-[2-(optionally substituted-3-indolyl)ethyl]amides (Flaugh, et al., *J. Med. Chem.*, 22, 63–69, (1979); Vakkuri et al., *Anal. Biochem.*, 142, 284–9, (1984); Stankov, et al., *Life Sci.*, 51, 479–485 (1992)); 2) substituted N-[2-(heteroaryl)ethyl]amines (EP 527,687 A2 130892); 3) N-[2-(optionally substituted-1-naphthyl)ethyl]amides (Yous, et al., *J. Med. Chem.*, 35, 1484–6 (1992); 4) N-[optionally substituted-1,2,3,4-tetrahydronaphth-2-yl]amides (Copinga, et al., *J. Med. Chem.*, 36, 2891–98 (1993); and 5) N-[(optionally substituted-1,2,3,4-tetrahydro-9H-carbazol-4-yl)methyl] amides (Garratt et al., *Bioorg. Med. Chem. Lett.*, 4, 1559–1564 (1994). The instant method is believed to provide a more efficacious (in terms of activity, side effect profile and duration of action) means for treating BPH than previously known. Further, the melatonin agonists used in the instant method are believed to be completely devoid of toxicity at the dosages required for treatment and, as such, a further object of the present invention is to provide a safe, efficacious, method of treating BPH.

Since the present invention provides a new method for treating BPH in mammals, pharmaceutical formulations suitable for such new method will be required. Accordingly, a further object of this invention is to provide pharmaceutical formulations suitable for use in the instantly claimed method.

Other objects, features and advantages of the present invention will become apparent from the subsequent description and the appended claims.

SUMMARY OF THE INVENTION

As noted above, the present invention provides a method of preventing or treating BPH in a male mammal suffering from or susceptible to such disorder which comprises administering to said male mammal an effective amount of a melatonin agonist. One such melatonin agonist is a compound of Formula (I)

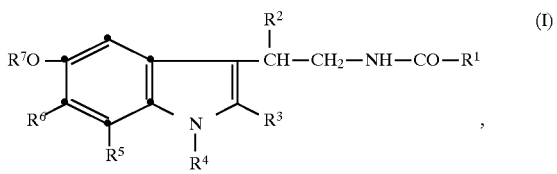

wherein
$R^1$ is hydrogen, $C_1$–$C_4$ alkyl or $C_1$–$C_4$ alkoxy;
$R^2$ is hydrogen or $C_1$–$C_4$ alkyl;
$R^3$ is hydrogen, $C_1$–$C_4$ alkyl, phenyl or substituted phenyl;
$R^4$ is hydrogen, haloacetyl, $C_1$–$C_5$ alkanoyl, benzoyl or benzoyl substituted with halo or methyl;
$R^5$ and $R^6$ are each individually hydrogen or halo; and
$R^7$ is hydrogen or $C_1$–$C_4$ alkyl.

DETAILED DESCRIPTION OF THE INVENTION

The following definitions refer to the various terms used above and throughout the disclosure.

The term "halo" refers to fluoro, chloro, bromo and iodo.

The term "$C_1$–$C_4$ alkyl" refers to the straight and branched aliphatic radicals of 1–4 carbon atoms including methyl, ethyl, propyl, isopropyl, n-butyl, isobutyl, sec-butyl and tert-butyl.

The term "$C_1$–$C_4$ alkoxy" includes the straight and branched aliphatic ether radicals of 1–4 carbon atoms such as methoxy, ethoxy, propoxy, isopropoxy, n-butoxy, isobutoxy, sec-butoxy and tert-butoxy.

The term "haloacetyl" refers to chloroacetyl, bromoacetyl, fluoroacetyl and iodoacetyl.

The term "$C_1$–$C_5$ alkanoyl" includes, for example, formyl, acetyl, propionyl, butyryl, α-methylpropionyl, valeryl, α-methyl-butyryl, β-methylbutyryl and pivaloyl.

The term "benzoyl substituted with halo" defines mono- and di-halo benzoyl groups. Specific mono-halo benzoyl groups are chlorobenzoyl, bromobenzoyl, fluorobenzoyl and iodobenzoyl.

Di-halo benzoyl groups include those in which both halo substituents are the same. Typical di-halo benzoyl groups include 2,4-dichlorobenzoyl, 3,4-dibromobenzoyl, 2,5-difluorobenzoyl and 2,6-diiodobenzoyl.

The term "benzoyl substituted with methyl" contemplates methylbenzoyl, dimethylbenzoyl and trimethylbenzoyl.

The term "substituted phenyl" refers to a phenyl ring which is substituted with one or two substituents selected from the group consisting of halo, $C_1$–$C_4$ alkyl or $C_1$–$C_4$ alkoxy. Examples of such term, therefore, include 4-chlorophenyl, 2-fluorophenyl, 3-iodophenyl, 4-bromophenyl, 3,4-dibromophenyl, 4-methylphenyl, 2-ethylphenyl, 3-n-propylphenyl, 4-isopropyl-phenyl, 4-n-butylphenyl, 3-t-butylphenyl, 4-sec-butylphenyl, 3,4-dimethylphenyl, 4-methoxyphenyl, 3-ethoxyphenyl, 2-n-propylphenyl, 4-isopropoxyphenyl, 3-isobutoxyphenyl, 4-t-butoxyphenyl, 3-ethoxy-4-methoxyphenyl and the like.

While all of the compounds of Formula I are believed to be useful for the method of preventing and treating BPH presented herein, certain of such compounds are preferred for such use. Preferred compounds of Formula I for use in the instantly claimed method include those compounds wherein $R^1$ is $C_1$–$C_4$ alkyl (especially methyl), $R^3$ is hydrogen or $C_1$–$C_4$ alkyl (especially methyl) and $R^4$ is hydrogen.

Of such preferred compounds, particularly preferred compounds include those wherein $R^2$ and $R^7$ are each independently $C_1$–$C_4$ alkyl (preferably methyl). The most preferred compounds for use in the method of the present invention include N-[2-methyl-2-(5-methoxy-6-fluoroindol-3-yl)ethyl]acetamide, N-[2-ethyl-2-(5-methoxy-6-chloroindol-3-yl)ethyl]acetamide, N-[2-methyl-2-(5-methoxy-6,7-dichloroindol-3-yl)ethyl]acetamide and N-[2-methyl-2-(5-methoxy-6-chloroindol-3-yl)ethyl]acetamide. The latter compound is especially preferred for purposes of the present invention.

Those compounds employed in the method of the present invention wherein $R^2$ is $C_1$–$C_4$ alkyl have an asymmetric center at the carbon atom to which such $R^2$ substituent is attached (i.e., the β-carbon atom). As such, such $R^2$ substituted compounds can exist as either a racemic mixture or as individual stereoisomers. All such types of compounds are contemplated for use in the method of the present invention.

The following list illustrates representative compounds suitable for use in the present invention.

N-[2-methyl-2-(5-methoxy-6-chloroindol-3-yl)ethyl]-acetamide

N-[2-methyl-2-(5-methoxy-6-fluoroindol-3-yl)ethyl]-acetamide

N-[2-ethyl-2-(5-methoxy-6-fluoroindol-3-yl)ethyl]-acetamide

N-[2-ethyl-2-(5-methoxy-6-chloroindol-3-yl)ethyl]-acetamide

N-[2-isopropyl-2-(5-methoxy-6-chloroindol-3-yl)ethyl]-acetamide

N-[2-isopropyl-2-(5-methoxy-6-fluoroindol-3-yl)ethyl]-acetamide

N-[2-methyl-2-(5-methoxy-6-bromoindol-3-yl)ethyl]-formamide

N-[2-butyl-2-(5-methoxy-6-bromoindol-3-yl)ethyl]-formamide

N-[2-ethyl-2-(5-propoxy-6-chloroindol-3-yl)ethyl]-formamide

N-[2-propyl-2-(5-isopropoxy-6-iodoindol-3-yl)ethyl]-formamide

N-[2-methyl-2-(5-methoxy-6-chloroindol-3-yl)ethyl]-propionamide

N-[2-ethyl-2-(5-methoxy-6-fluoroindol-3-yl)ethyl]-propionamide

N-[2-methyl-2-(5-ethoxy-6-bromoindol-3-yl)ethyl]-propionamide

N-[2-methyl-2-(5-ethoxy-6-fluoroindol-3-yl)ethyl]-butyramide

N-[2-propyl-2-(5-butoxy-6-chloroindol-3-yl)ethyl]-butyramide

N-[2-methyl-2-(5-methoxy-6-chloroindol-3-yl)ethyl]-butyramide

N-[2-methyl-2-(5-methoxy-7-chloroindol-3-yl)ethyl]-acetamide

N-[2-methyl-2-(5-methoxy-7-fluoroindol-3-yl)ethyl]-acetamide

N-[2-ethyl-2-(5-methoxy-7-chloroindol-3-yl)ethyl]-acetamide

N-[2-propyl-2-(5-methoxy-7-bromoindol-3-yl)ethyl]-acetamide

N-[2-ethyl-2-(5-t-butoxy-7-chloroindol-3-yl)ethyl]-formamide

N-[2-ethyl-2-(5-ethoxy-7-iodoindol-3-yl)ethyl]-formamide

N-[2-methyl-2-(5-isopropoxy-7-chloroindol-3-yl)ethyl]-formamide

N-[2-methyl-2-(5-methoxy-7-bromoindol-3-yl)ethyl]-propionamide

N-[2-ethyl-2-(5-propoxy-7-chloroindol-3-yl)ethyl]-propionamide

N-[2-methyl-2-(5-s-butoxy-7-fluoroindol-3-yl)ethyl]-propionamide

N-[2-methyl-2-(5-methoxy-7-chloroindol-3-yl)ethyl]-butyramide

N-[2-butyl-2-(5-ethoxy-7-chloroindol-3-yl)ethyl]-butyramide

N-[2-ethyl-2-(5-methoxy-7-fluoroindol-3-yl)ethyl]-butyramide

N-[2-methyl-2-(5-methoxy-6,7-dichloroindol-3-yl)ethyl]acetamide

N-[2-ethyl-2-(5-methoxy-6,7-dichloroindol-3-yl)ethyl]acetamide

N-[2-isopropyl-2-(5-methoxy-6,7-dichloroindol-3-yl)ethyl]acetamide

N-[2-methyl-2-(5-isopropoxy-6,7-dichloroindol-3-yl)ethyl]acetamide

N-[2-methyl-2-(5-methoxy-6,7-difluoroindol-3-yl)ethyl]acetamide

N-[2-propyl-2-(5-methoxy-6,7-difluoroindol-3-yl)ethyl]acetamide

N-[2-ethyl-2-(5-butoxy-6,7-difluoroindol-3-yl)ethyl]acetamide

N-[2-methyl-2-(5-methoxy-6-chloro-7-fluoroindol-3-yl)ethyl]acetamide

N-[2-methyl-2-(5-methoxy-6-chloro-7-bromoindol-3-yl)ethyl]acetamide

N-[2-methyl-2-(5-methoxy-6-fluoro-7-chloroindol-3-yl)ethyl]acetamide

N-[2-methyl-2-(5-ethoxy-6-bromo-7-iodoindol-3-yl)ethyl]acetamide

N-[2-ethyl-2-(5-ethoxy-6-chloro-7-fluoroindol-3-yl)ethyl]acetamide

N-[2-isopropyl-2-(5-t-butoxy-6-chloro-7-fluoroindol-3-yl)ethyl]acetamide

N-[2-ethyl-2-(5-butoxy-6-bromo-7-chloroindol-3-yl)ethyl]acetamide

N-[2-methyl-2-(5-methoxy-6,7-dichloroindol-3-yl)ethyl]formamide

N-[2-methyl-2-(5-methoxy-6,7-dibromoindol-3-yl)ethyl]formamide

N-[2-t-butyl-2-(5-methoxy-6-chloro-7-fluoroindol-3-yl)ethyl]formamide

N-[2-ethyl-2-(5-ethoxy-6-fluoro-7-bromoindol-3-yl)ethyl]formamide

N-[2-ethyl-2-(5-s-butoxy-6-fluoro-7-chloroindol-3-yl)ethyl]formamide

N-[2-methyl-2-(5-methoxy-6,7-dichloroindol-3-yl)ethyl]propionamide

N-[2-ethyl-2-(5-methoxy-6,7-dichloroindol-3-yl)ethyl]propionamide

N-[2-propyl-2-(5-isopropoxy-6-chloro-7-fluoroindol-3-yl)ethyl]propionamide

N-[2-methyl-2-(5-methoxy-6-bromo-7-iodoindol-3-yl)ethyl]propionamide

N-[2-methyl-2-(5-ethoxy-6-bromo-7-chloroindol-3-10 yl)ethyl]propionamide

N-[2-methyl-2-(5-methoxy-6,7-difluoroindol-3-yl)ethyl]butyramide

N-[2-ethyl-2-(5-methoxy-6-fluoro-7-chloroindol-3-yl)ethyl]butyramide

N-[2-isopropyl-2-(5-methoxy-6,7-dibromoindol-3-yl)ethyl]butyramide

N-[2-isopropyl-2-(5-butoxy-6-bromo-7-chloroindol-3-yl)ethyl]butyramide

N-[2-ethyl-2-(5-methoxy-6,7-dichloro-3-yl)ethyl]-butyramide

N-[2-methyl-2-(1-acetyl-5-methoxy-6-chloroindol-3-yl)ethyl]acetamide

N-[2-butyl-2-(1-acetyl-5-methoxy-6-fluoroindol-3-yl)ethyl]acetamide

N-[2-ethyl-2-(1-acetyl-5-isopropoxy-6-chloro-7-fluoroindol-3-yl)ethyl]acetamide

N-[2-methyl-2-(1-propionyl-5-methoxy-6-fluoroindol-3-yl)ethyl]acetamide

N-[2-methyl-2-(1-propionyl-5-ethoxy-6,7-dichloroindol-3-yl)ethyl]acetamide

N-[2-ethyl-2-(1-propionyl-5-butoxy-7-chloroindol-3-yl)ethyl]acetamide

N-[2-methyl-2-(1-pivaloyl-5-ethoxy-6-bromoindol-3-yl)ethyl]formamide

N-[2-propyl-2-(1-chloroacetyl-5-methoxy-6-bromo-7-fluoroindol-3-yl)ethyl]propionamide N-[2-methyl-2-(1-bromoacetyl-5-ethoxy-7-chloroindol-3-yl)ethyl]butyramide N-[2-ethyl-2-(1-valeryl-5-isopropoxy-6,7-dichloroindol-3-yl)ethyl]acetamide N-[2-methyl-2-(1-butyryl-5-methoxy-6-chloroindol-3-yl)ethyl]acetamide N-[2-ethyl-2-(1-benzoyl-5-t-butoxy-7-bromoindol-3-yl)ethyl]formamide N-[[2-isopropyl-2-[1-(4-chlorobenzoyl)-5-methoxy-7-fluoroindol-3-yl]ethyl]]formamide N-[[2-methyl-2-[1-(4-bromobenzoyl)-5-ethoxy-6,7-dichloroindol-3-yl]ethyl]]propionamide N-[[2-ethyl-2-[1-(2,4-dichlorobenzoyl)-5-methoxy-7-bromoindol-3-yl]ethyl]]propionamide N-[[2-methyl-2-[1-(2,4-difluorobenzoyl)-5-propoxy-6-chloroindol-3-yl]ethyl]]formamide N-[[2-methyl-2-[1-(4-iodobenzoyl)-5-ethoxy-6-fluoro-7-chloroindol-3-yl]ethyl]]acetamide N-[[2-ethyl-2-[1-(2-methylbenzoyl)-5-methoxyindol-3-yl]ethyl]]propionamide N-[[2-methyl-2-[1-(4-fluorobenzoyl)-5-ethoxyindol-3-yl]ethyl]]formamide N-[[2-methyl-2-[1-(2,6-dimethylbenzoyl)-5-methoxy-7-fluoroindol-3-yl]ethyl]]formamide N-[[2-ethyl-2-[1-(2,6-dimethylbenzoyl)-5-ethoxyindol-3-yl]ethyl]]acetamide N-[[2-ethyl-2-[1-(2,4,6-trimethoxybenzoyl)-5-methoxy-6-chloroindol-3-yl]ethyl]]propionamide N-[[2-methyl-2-[1-(2,4,6-trimethoxybenzoyl)-5-methoxyindol-3-yl]ethyl]]formamide N-[2-ethyl-2-(1-pivaloyl-5-isopropoxyindol-3-yl)ethyl]acetamide N-[2-methyl-2-(1-chloroacetyl-5-methoxyindol-3-yl)ethyl]butyramide N-[2-methyl-2-(5-methoxyindol-3-yl)ethyl]acetamide N-[2-ethyl-2-(5-methoxyindol-3-yl)ethyl]acetamide N-[2-ethyl-2-(5-methoxyindol-3-yl)ethyl]propionamide N-[2-methyl-2-(5-propoxyindol-3-yl)ethyl]formamide N-[2-methyl-2-(5-s-butoxyindol-3-yl)ethyl]butyramide N-[2-ethyl-2-(5-ethoxyindol-3-yl)ethyl]propionamide N-[2-methyl-2-(5-ethoxyindol-3-yl)ethyl]formamide N-[2-isopropyl-2-(5-methoxyindol-3-yl)ethyl]acetamide N-[2-ethyl-2-(5-methoxyindol-3-yl)ethyl]formamide N-[2-(5-methoxy-6-chloroindol-3-yl)ethyl]acetamide N-[2-(5-methoxy-6-fluoroindol-3-yl)ethyl]acetamide N-[2-(5-methoxy-6-bromoindol-3-yl)ethyl]formamide N-[2-(5-methoxy-6-iodoindol-3-yl)ethyl]propionamide N-[2-(5-methoxy-6-chloroindol-3-yl)ethyl]-n-butyramide N-[2-(2-methyl-5-methoxy-6-bromoindol-3-yl)ethyl]-acetamide N-[2-(2-ethyl-5-methoxy-6-chloroindol-3-yl)ethyl]-acetamide N-[2-(2-n-propyl-5-methoxy-6-chloroindol-3-yl)ethyl]-formamide N-[2-(2-n-butyl-5-methoxy-6-chloroindol-3-yl)ethyl]-formamide N-[2-(2-ethyl-5-methoxy-6-iodoindol-3-yl)ethyl]-propionamide N-[2-(2-isopropyl-5-methoxy-6-fluoroindol-3-yl)ethyl]-α-methylpropionamide N-[2-(2-phenyl-5-methoxy-6-chloroindol-3-yl)ethyl]-formamide N-[2-(2-phenyl-5-methoxy-6-bromoindol-3-yl)ethyl]-acetamide N-[2-(2-phenyl-5-methoxy-6-iodoindol-3-yl)ethyl]-propionamide N-[2-((2-(4-chlorophenyl)-5-methoxy-6-chloroindol-3-yl))ethyl]formamide N-[2-((2-(3-fluorophenyl)-5-methoxy-6-bromoindol-3-yl))ethyl]acetamide N-[2-((2-(2-fluorophenyl)-5-methoxy-6-chloroindol-3-yl))ethyl]propionamide N-[2-((2-(4-methylphenyl)-5-methoxy-6-bromoindol-3-yl))ethyl]formamide N-[2-((2-(3-ethylphenyl)-5-methoxy-6-fluoroindol-3-yl))ethyl]butyramide N-[2-((2-(4-n-propylphenyl)-5-methoxy-6-chloroindol-3-yl))ethyl]formamide N-[2-((2-(3-isopropylphenyl)-5-methoxy-6-fluoroindol-3-yl))ethyl]acetamide N-[2-((2-(4-methoxyphenyl)-5-methoxy-6-chloroindol-3-yl))ethyl]propionamide N-[2-((2-(3-ethoxyphenyl)-5-methoxy-6-bromoindol-3-yl))ethyl]acetamide N-[2-((2-(3-n-propoxyphenyl)-5-methoxy-6-fluoroindol-3-yl))ethyl]acetamide N-[2-((2-(4-t-butoxyphenyl)-5-methoxy-6-chloroindol-3-yl))ethyl]formamide N-[2-((2-(3-n-butoxyphenyl)-5-methoxy-6-chloroindol-3-yl))ethyl]acetamide N-[2-(1-acetyl-5-methoxy-6-chloroindol-3-yl)ethyl]acetamide N-[2-(1-propionyl-5-methoxy-6-fluoroindol-3-yl)ethyl]acetamide N-[2-(1-pivaloyl-5-methoxy-6-bromoindol-3-yl)ethyl]formamide N-[2-(1-chloroacetyl-5-methoxy-6-iodoindol-3-yl)ethyl]propionamide N-[2-(1-bromoacetyl-5-methoxy-6-chloroindol-3-yl)ethyl]-n-butyramide N-[2-(1-valeryl-2-methyl-5-methoxy-6-bromoindol-3-yl)ethyl]acetamide N-[2-(1-butyryl-2-ethyl-5-methoxy-6-chloroindol-3-yl)ethyl]acetamide N-[2-(1-benzoyl-2-n-propyl-5-methoxy-6-chloroindol-3-yl) ethyl]formamide N-[[2-[1-(4-chlorobenzoyl)-2-n-butyl-5-methoxy-6-chloroindol-3-yl]ethyl]]formamide N-[[2-[1-(4-bromobenzoyl)-2-ethyl-5-methoxy-6-iodoindol-3-yl]ethyl]]propionamide N-[[2-[1-(2,4-dichlorobenzoyl)-2-isopropyl-5-methoxy-6-fluoroindol-3-yl]ethyl]]-α-methylpropionamide N-[[2-[1-(2,4-difluorobenzoyl)-2-phenyl-5-methoxy-6-chloroindol-3-yl]ethyl]]formamide N-[[2-[1-(4-iodobenzoyl)-2-phenyl-5-methoxy-6-bromoindol-3-yl]ethyl]]acetamide N-[[2-[1-(2-methylbenzoyl)-2-phenyl-5-methoxy-6-iodoindol-3-yl]ethyl]]propionamide N-[[2-[1-(2,6-dimethylbenzoyl)-2-(4-chloro-phenyl)-5-methoxy-6-chloroindol-3-yl]ethyl]]formamide N-[[2-[1-(2,4,6-trimethylbenzoyl)-2-(3-fluorophenyl)-5-methoxy-6-bromoindol-3-yl]ethyl]]acetamide N-[2-(1-pivaloyl-5-methoxy-6-chloroindol-3-yl)ethyl]acetamide N-[2-(1-chloroacetyl-5-methoxy-6-chloroindol-3-yl)ethyl]acetamide N-[[2-[1-(4-chlorobenzoyl)-5-methoxy-6-chloroindol-3-yl]ethyl]]acetamide N-[[2-[1-(2,4-dichlorobenzoyl)-5-methoxy-6-chloroindol-3-yl]ethyl]]acetamide N-[[2-[1-(2-methylbenzoyl)-5-methoxy-6-chloroindol-3-yl]ethyl]]acetamide N-[[2-[1-(2,6-dimethylbenzoyl)-5-methoxy-6-chloroindol-3-yl]ethyl]]acetamide N-[[2-[1-(2,4,6-trimethylbenzoyl)-5-methoxy-6-chloroindol-3-yl]ethyl]]acetamide N-[2-(5-methoxy-6,7-dichloroindol-3-yl)ethyl]acetamide N-[2-(2-methyl-5-methoxy-6,7-difluoroindol-3-yl)ethyl]acetamide N-[2-(2-methyl-5-methoxy-6-fluoro-7-chloroindol-3-yl)ethyl]acetamide N-[2-(5-methoxy-6,7-dichloroindol-3-yl)ethyl]-propionamide N-[2-(5-methoxy-6,7-difluoroindol-3-yl)ethyl]-isobutyramide N-[2-(2-methyl-5-methoxy-6,7-dichloroindol-3-yl)-ethyl]-n-butyramide; and the like.

The compounds employed in the method of this invention are known in the art or can be made by methods described in the art. Representative publications which teach the preparation of compounds of Formula I include U.S. Pat. Nos. 4,087,444; 4,614,807; and 4,997,845. The teaching of all such patents is hereby incorporated by reference.

Melatonin agonists, as used in this invention, are useful in treating benign prostatic hypertrophy (BPH) in male mammals. Diseases of the prostate are some of the most common in the human male. BPH occurs in over 80% of the male population before the age of 80 and 25% will require surgery at some time to alleviate the most common symptom, urinary obstruction. The cause of BPH is not well defined, but is believed to be mediated by the effect of androgens and their metabolites, particularly dihydrotestosterone. While the role of melatonin in BPH is unknown, evidence for melatonin receptors in the human prostate has been recently presented (EP 565291 A1 931013).

As discussed above, melatonin agonists are useful in treating BPH in mammals. Such method comprises administering to a mammal (preferably a human) in need of such treatment a sufficient amount of one or more melatonin agonists so as to achieve the therapeutic intervention desired. The compounds can be administered by a variety of routes including the oral, rectal, transdermal, subcutaneous, intravenous, intramuscular or intranasal routes. The oral and transdermal routes are preferred. No matter what route of administration is chosen, such administration is accomplished by means of pharmaceutical compositions which are prepared by techniques well known in the pharmaceutical sciences.

In making these compositions, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 0.1 to about 100 mg, more usually about 10 to about 50 mg, of the active ingredient. The term "unit dosage form" refers to physically discrete units suitable as unitary dosages for human subjects and other mammals, each unit containing a predetermined quantity of active material calculated to produce the desired therapeutic or prophylactic effect, in association with one or more suitable pharmaceutical diluents, excipients or carriers.

The compounds employed in the method of the present invention are effective over a dosage range of about 0.1 mg/day to about 100 mg/day for preventing or treating BPH. Thus, as used herein, the term "effective amount" refers to a dosage range of from about 0.1 to about 100 mg of active ingredient per day. In the treatment of adult humans, the range of about 10 to about 50 mg of active ingredient per day, in single or divided doses, is preferred.

In some patients, the amount of melatonin agonist required to treat BPH may be greater than 100 mg/day. In these patients, who are mostly elderly in nature, the pineal gland is no longer capable of secreting its principal hormone, melatonin.

The following formulation examples may employ as active ingredient any melatonin agonist. The examples are illustrative only and are not intended to limit the scope of the invention in any way.

EXAMPLE 1

Hard gelatin capsules suitable for treating or preventing BPH are prepared using the following ingredients:

| (mg/capsule) | Quantity |
| --- | --- |
| (±)-N-[2-methyl-2-(5-methoxy)-6-chloroindol-3-yl)ethyl]acetamide | 100 |
| Starch dried | 200 |
| Magnesium stearate | 10 |

The above ingredients are mixed and filled into hard gelatin capsules in 310 mg quantities.

EXAMPLE 2

A tablet suitable for treating or preventing BPH is prepared using the ingredients below:

| (mg/tablet) | Quantity |
| --- | --- |
| (−)-N-[2-methyl-2-(5-methoxy)-6-chloroindol-3-yl)ethyl]acetamide | 5 |
| Cellulose, microcrystalline | 400 |
| Silicon dioxide | 10 |
| Stearic acid | 5 |

The components are blended and compressed to form tablets each weighing 420 mg.

EXAMPLE 3

An aerosol solution suitable for treating or preventing BPH is prepared containing the following components:

| | Weight |
| --- | --- |
| (±)-N-[2-methyl-2-(5-methoxy-6-fluoroindol-3-yl)ethyl]acetamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. Valve units are then fitted to the container.

EXAMPLE 4

Tablets suitable for treating or preventing BPH, each containing 1 mg of active ingredient, are made up as follows:

| | |
| --- | --- |
| (+)-N-[2-methyl-2-(5-methoxy)-6-chloroindol-3-yl)ethyl]acetamide | 1 mg |
| Starch | 44 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 90 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 90 mg.

EXAMPLE 5

Capsules suitable for treating or preventing BPH, each containing 10 mg of medicament, are made as follows:

| | |
|---|---|
| (−)-N-[2-methyl-2-(5-methoxy)-6,7-dichloroindol-3-yl)ethyl]acetamide | 50 mg |
| Starch | 59 mg |
| Microcrystalline cellulose | 59 mg |
| Magnesium stearate | mg |
| Total | 170 mg |

The active ingredient, cellulose, starch and magnesium stearate are blended, passed through a No. 45 mesh U.S. sieve, and filled into hard gelatin capsules in 170 mg quantities.

EXAMPLE 6

Suppositories suitable for treating or preventing BPH, each containing 20 mg of active ingredient, are made as follows:

| | |
|---|---|
| (±)-N-[2-ethyl-2-(5-methoxy-6-chloroindol-3-yl)ethyl]acetamide | 20 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions suitable for treating or preventing BPH, each containing 5 mg of medicament per 5 ml dose, are made as follows:

| | |
|---|---|
| (±)-N-[2-methyl-2-(5-methoxy-6-chloroindol-3-yl)ethyl]acetamide | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules suitable for use in treating or preventing BPH, each containing 15 mg of medicament, are made as follows:

| | |
|---|---|
| (±)-N-[2-methyl-2-(5-methoxy-6,7-dichloroindol-3-yl)ethyl]acetamide | 15 mg |
| Starch | 164 mg |
| Microcrystalline cellulose | 164 mg |
| Magnesium stearate | 22 mg |
| Total | 365 mg |

The active ingredient, cellulose, starch and magnesium stearate are blended, passed through a No. 45 mesh U.S. sieve, and filled into hard gelatin capsules in 365 mg quantities.

We claim:

1. A method for the treatment of benign prostatic hyperplasia in mammals comprising administration to a mammal in need of such treatment an effective dose of R-(+)-N-[2-methyl-2-(5-methoxy-6-chloroindol-3-yl)ethyl]acetamide.

2. The method of claim 1 wherein the mammal is a human.

* * * * *